United States Patent [19]

Nakajima et al.

[11] Patent Number: 4,944,189
[45] Date of Patent: Jul. 31, 1990

[54] ULTRASONIC SPECKLE VELOCITY MEASUREMENT METHOD AND APPARATUS

[75] Inventors: Masato Nakajima; Takashi Ito, both of Tokyo, Japan

[73] Assignee: Aloka Co., Ltd., Tokyo, Japan

[21] Appl. No.: 275,728

[22] Filed: Nov. 23, 1988

[30] Foreign Application Priority Data

Nov. 30, 1987 [JP] Japan ................................ 62-301736

[51] Int. Cl.$^5$ .............................................. G01F 1/66
[52] U.S. Cl. ............................... 73/861.25; 73/861.04; 128/660.01
[58] Field of Search ......................... 73/861.04, 861.25; 128/660, 660.01, 660.07, 660.08, 661.01

[56] References Cited

U.S. PATENT DOCUMENTS

| | | | |
|---|---|---|---|
| 4,103,679 | 8/1978 | Aronson | 73/861.25 |
| 4,122,713 | 10/1978 | Stasz et al. | 73/861.25 |
| 4,245,211 | 1/1981 | Kao | 382/7 |
| 4,744,367 | 5/1988 | Kodama et al. | 73/861.25 |
| 4,790,321 | 12/1988 | Miwa et al. | 128/660.07 |

Primary Examiner—Hezron E. Williams
Assistant Examiner—Rose M. Finley
Attorney, Agent, or Firm—Koda & Androlia

[57] ABSTRACT

An ultrasonic speckle velocity measurement method and apparatus that uses the transmission and reception of ultrasonic waves to detect the velocity of moving members comprised of random scattering bodies. The ultrasonic wave transmitted toward a moving measurement object containing a large number of microscopic scattering bodies, and echo signlas reflected by the measurement object are received. If, for example, the scattering bodies are blood corpuscles, the blood flow can be regarded as a random aggregation of these corpuscles, in which case the echo signal received will be the product of the random interference between waves scattered by individual corpuscles, and as such the blood flow velocity can be estimated from time-based fluctuation in the amplitude of the echo signals. Thus, the time-based fluctuation in the received echo signals is detected from, for example, the envelope signal thereof and frequency-analyzed, and from the fluctuation frequency thereof the velocity is obtained. Accordingly, without using the conventional untrasonic Doppler method is it possible to detect velocity and, in particular, to measure with accuracy even low velocities, and it is also possible to detect the velocity of moving members regardless of the direction in which the ultrasonic beam is transmitted.

9 Claims, 8 Drawing Sheets

ULTRASONIC SPECKLE VELOCITY MEASUREMENT METHOD AND APPARATUS

BACKGROUND OF THE INVENTION

1. Field of the Invention

The present invention relates to an ultrasonic speckle velocity measurement method and apparatus, more particularly to an ultrasonic speckle velocity measurement method and apparatus for detecting the velocities of moving members comprised of random scattering bodies, within a subject under examination, not through the detection of frequency shift information produced by the Doppler effect but by a novel method which uses amplitude fluctuations (speckles) in the received signals resulting from random interference between the ultrasonic waves scattered by the scattering bodies.

2. Description of the Prior Art

The ultrasonic Doppler method is a well-known method of measuring the velocity of moving members, such as for example the blood flow, in a subject. The ultrasonic Doppler method utilizes the fact that the motion of a moving member produces a frequency shift in the carrier frequency of a transmitted ultrasonic wave, i.e., the frequency shift corresponding to the velocity of the moving member. Therefore, by detecting the frequency shift from the center frequency of the reflected echo signal, the velocity distribution of the moving member can be displayed in real time on a display screen or the like.

However, with this type of ultrasonic Doppler method it is difficult to measure the velocity of moving members that are moving at a relatively low velocity. That is, with the ultrasonic Doppler method it is the frequency shift in the carrier frequency of the echo signal that is detected, but in the case of a moving member that is moving at a low velocity, the degree of frequency shift is extremely small, and detecting this small degree of frequency shift from the echo signal, which is obtained as a time-series signal, is extremely difficult.

Another drawback when the Doppler effect is utilized is that it is only possible to measure the velocity of the movement of a member which includes velocity components indicating a movement toward or away from the direction in which the ultrasonic wave is transmitted. The method cannot detect the movement velocity of a reflective member that is moving in a direction perpendicular to the ultrasonic wave, for example, when a single transducer is being used for transmitting and receiving the ultrasonic wave.

SUMMARY OF THE INVENTION

In view of the above-mentioned problems, the primary object of the present invention is to provide an ultrasonic speckle velocity measurement method and apparatus that enable the velocity of moving member to be detected without using the conventional Doppler method.

Another object of the present invention is to provide an ultrasonic speckle velocity measurement method and apparatus that enable the velocity of slow-moving members to be measured accurately.

A further object of the present invention is to provide an ultrasonic speckle velocity measurement method and apparatus that enable the velocity of members moving in a direction perpendicular to the ultrasonic wave to be detected.

In order to attain these objects, the ultrasonic speckle velocity measurement method according to the present invention comprises a transmission step in which an ultrasonic wave is transmitted toward a moving measurement object that includes a large number of microscopic scattering bodies; a receiving step in which an echo signal reflected from the measurement object is received; an amplitude detection step in which time-based fluctuation in amplitude of received echo signals is detected; a frequency analysis step in which the time-based fluctuation in amplitude is frequency-analyzed and a fluctuation frequency that shows the degree of said fluctuation is detected; and a velocity conversion step in which the velocity is measured from this fluctuation frequency.

The ultrasonic speckle velocity measurement apparatus according to the present invention comprises a transmission section for transmitting an ultrasonic continuous wave toward a measurement object that includes a large number of microscopic scattering bodies; a receiving section for receiving echo signals reflected back from the measurement object; an envelope detection section that amplifies the output of the receiving section and detects the envelope of the echo signals; a frequency analysis section that frequency analyzes the time-based fluctuation of the envelope output by the envelope detection section and detects the envelope fluctuation frequency; and a velocity conversion section that converts frequency values output from the frequency analysis section to velocities.

The ultrasonic speckle velocity measurement apparatus according to the present invention further comprises a transmission section for transmitting an ultrasonic pulsed wave toward a measurement object that includes a large number of microscopic scattering bodies; a receiving section for receiving echo signals reflected back from the measurement object; an envelope detection section that amplifies the output of the receiving section and obtains the envelope of the echo signals, and by sampling-holding of selected signals in the envelope detects time-based envelope amplitude fluctuations at a selected location within the subject; a frequency analysis section that frequency analyzes the time-based fluctuations of the envelope output by the envelope detection section and detects the envelope fluctuation frequency; and a velocity conversion section that converts frequency values output from the frequency analysis section to velocities.

Principle of the Invention

Figure 6:
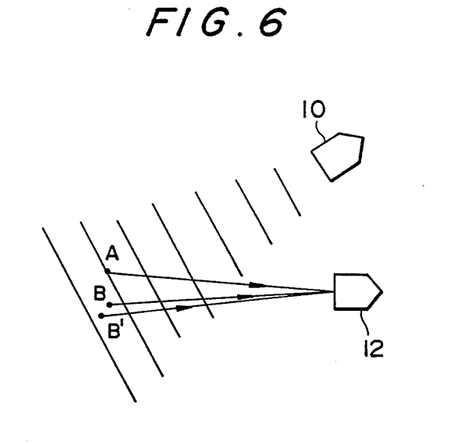
FIG. 6 is an explanatory diagram showing the state of interference between waves scattered by the microscopic scattering bodies.
Figure 7:
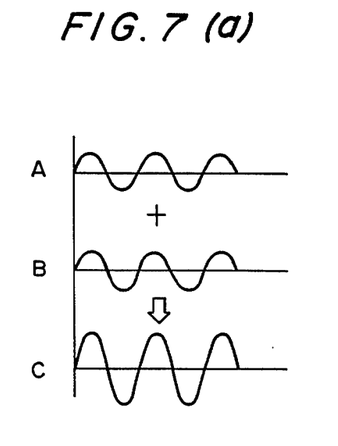
FIG. 7 is a waveform diagram showing the composite state of reflected echoes in the case of interference between waves scattered by the microscopic scattering bodies.

As shown in FIG. 6, when two scattering bodies A and B in a certain region are subjected to ultrasonic waves transmitted by a transmitter 10, because the length of the propagation path from the transmitter 10 to a receiver 12 via scattering body A is the same as the length of the propagation path via scattering body B, the reflected echo waves from the scattering bodies A and B are received as composite echo signals A and B of the same phase, as shown in FIG. 7 (a), the reflected echo signal C obtained by the receiver 12 being doubled in amplitude without undergoing any change in phase.

On the other hand, when B has moved to B', the length of the propagation path becomes different, as a result of which, as shown in FIG. 7 (b), a composite is formed of the echo signals differing by ¼ wavelength, so that the reflected echo signal C' obtained by the receiver 12 differs in phase and amplitude from the reflected echo signal C of FIG. 7 (a). From this, it therefore follows that when the random scattering bodies move, the amplitude and phase of the composite reflected echo signals formed in accordance with the distribution state of the scattering bodies will differ.

Figure 8:
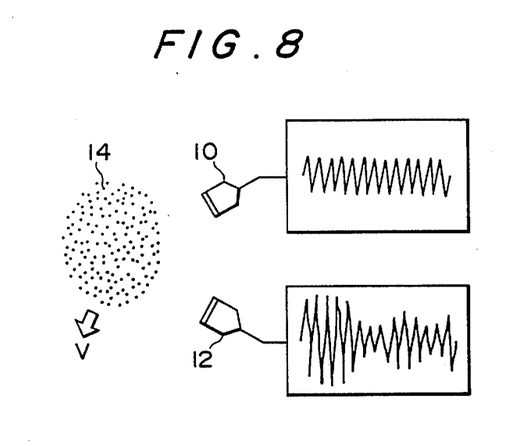
FIG. 8 is a concept diagram to explain when there is movement of random microscopic scattering bodies.

FIG. 8 shows the state of signal reception when the random scattering bodies 14 have moved at a prescribed velocity V. When an ultrasonic wave of a prescribed frequency and uniform amplitude is beamed at the scattering bodies 14 from the transmitter 10, the result of random interference between the ultrasonic waves scattered by the microscopic scattering bodies is that the waveform of an echo signal received at the receiver 12 shows fluctuations in amplitude. That is, the result of random interference of the ultrasonic waves is to give rise to amplitude fluctuations (speckles) in the received signal waveform that is obtained.

As echo signals are formed as the result of interference, as mentioned above the amplitude thereof is varied considerably according to the relative positional relationships of the microscopic scattering bodies. As such, when these scattering bodies 14 move at a certain velocity V, the amplitude of the received waveform fluctuates with time in accordance with the velocity V of the scattering bodies, and it becomes possible to estimate the velocity from the degree of fluctuation, i.e., from the degree of time-based change. In a living body, if for example blood corpuscles are considered as the scattering bodies, blood can be considered as an aggregation of these scattering bodies, in which case the echo signal received will be the result of interference between echo signals scattered by the individual corpuscles.

Thus, in the detected echo signal, the time-based fluctuations in amplitude are produced by changes in the relative positions of the scattering bodies, so that even if the direction of movement of the scattering bodies is perpendicular to the transmitted ultrasonic beam, it is possible to measure the velocity thereof. As such, with the principle of the present invention there is the advantage that, unlike in the case of the principle of the conventional ultrasonic Doppler method, there is no direction in which the velocity cannot be measured.

The principle of the present invention also enables the velocity of scattering bodies moving at very low speeds to be measured, in the form of low-frequency amplitude fluctuation frequency which shows the degree of time-based amplitude variation, enabling the detection of low velocities that cannot be detected with the conventional ultrasonic Doppler method.

This type of velocity measurement using speckle patterns is also employed in fields in which laser beams are used. However, this use consists of projecting a laser beam at a moving optical scatterer such as opaque glass, picking up the light scattered by the rough surface of the scatterer and obtaining the random interference pattern (speckle pattern) produced by the reflections of the laser light, the velocity of movement of the optical scatterer being measured from variations in the interference pattern.

Because with such speckle velocimetry using laser light the velocity is obtained as the result of interference of the light reflected from the surface of the object, it follows that such velocimetry cannot be used to measure the velocity of moving members within a subject.

The present inventors discovered that speckle can also be used for velocity measurement within a subject, and the result is the present invention that, based on the aforementioned principle, enables speckle velocity measurement of moving members within a living body.

Operation of the Invention

With the above arrangement, an ultrasonic wave is beamed at the measurement object formed of a large number of microscopic scattering bodies, the echo signals scattered by the measurement object are received, time-based amplitude fluctuations in the received echo signals are detected, and to show the degree of the fluctuations, the fluctuation frequency of the echo signal envelope, for example, is detected, and the fluctuation frequency is used to measure the velocity of the scattering bodies.

The results of experiments based on the above-described principle for measuring the velocity of movement will now be described.

Figure 9:
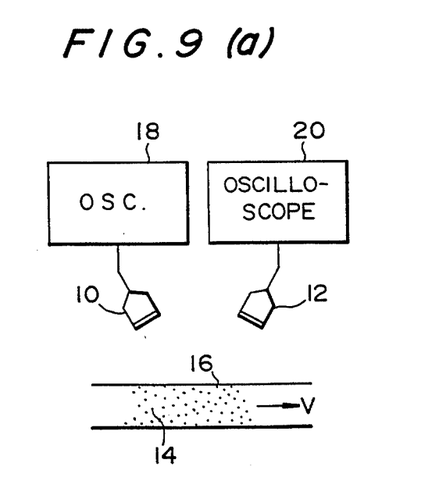
FIG. 9 is an explanatory diagram of the arrangement of an experimental apparatus for explaining the principle of the present invention, and a diagram of an echo signal obtained with the said apparatus.

For the experiments, as shown in FIG. 9 (a), water containing aluminum powder (with a mean particle diameter of 25μm) as the scattering bodies 14 was fed through an acrylic tube 16. An ultrasonic wave beam based on a fixed-frequency oscillation signal provided by an oscillator 18 was transmitted into the acrylic tube 16 by a transmitter 10. The reflected echoes were picked up by a receiver 12 and observed by means of an oscilloscope 20. Here, the aluminum powder scatterers can be regarded as scattering bodies analogous to blood corpuscles.

FIG. 9 (b) shows the echo signals thus obtained. The time-based fluctuation in echo signal amplitude can be obtained as fluctuation in the envelope of the echo signals.

As the parameter representing the degree of time-based amplitude variation, the peaks and troughs in the echo signal envelope per unit time were counted, using the oscilloscope 20, . to thereby detect the amplitude fluctuation frequency, which was measured while varying the flow velocity of the scattering bodies 14 in the acrylic tube 16.

Figure 10:
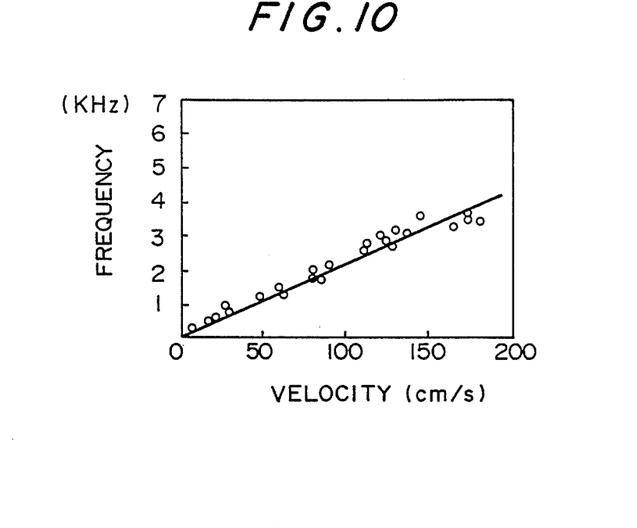
FIG. 10 is a graph showing the relationship between the fluctuation frequency of the echo signal envelope and the velocity of scattering bodies.

FIG. 10 shows the results. It can be seen that there is a proportional relationship between the amplitude fluctuation frequency of the echo signal and flow velocity, meaning that the flow velocity can be measured by detecting the amplitude fluctuation frequency.

Figure 11:
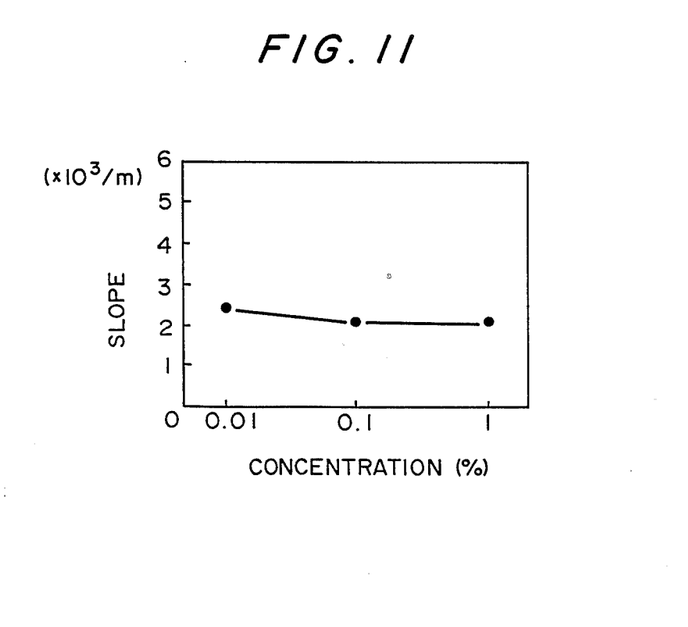
FIG. 11 is a graph showing the relationship between the slope of the fluctuation frequency of the echo signal envelope against the velocity of scattering bodies and the weight-percent (concentration) of aluminum powder used as scattering bodies.

FIG. 11 shows the results of an investigation into the relationship between the proportional constant (slope) and the weight-percent of the aluminum powder when the quantity of the scattering bodies 14 in the water was varied and measurements carried out in the same way as in the case of FIG. 10. As is apparent in the figure, the proportional constant (slope) between fluctuation frequency and flow velocity is substantially constant, independent of the quantity of aluminum powder, i.e., of the number of microscopic scattering bodies. Therefore, the velocity can be estimated by detecting the amplitude fluctuation frequency, which is unaffected by the number or concentration of scattering bodies.

DESCRIPTION OF PREFERRED EMBODIMENTS

A first embodiment of the present invention will now be described with reference to the drawings.

Figure 1:
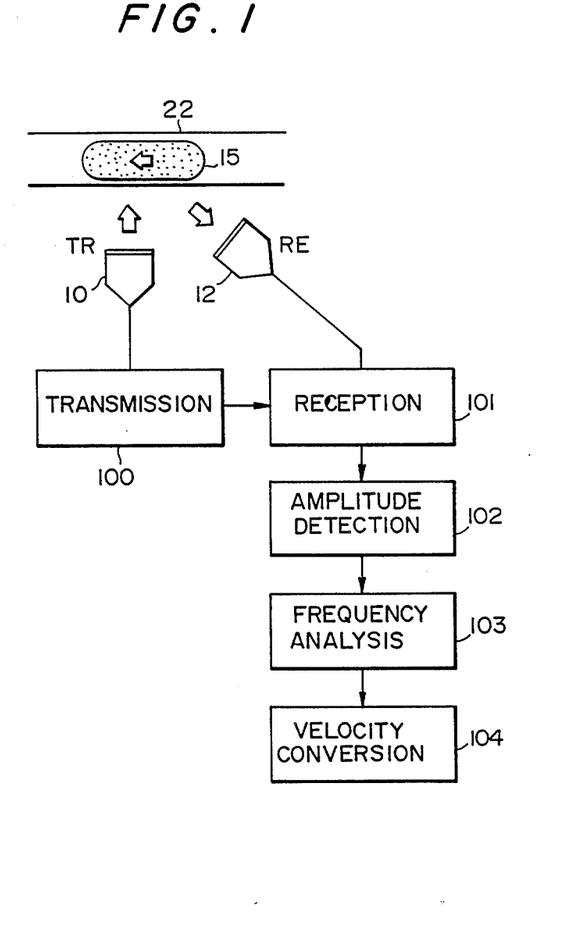
FIG. 1 is an explanatory diagram of the arrangement of a first embodiment of the ultrasonic speckle velocity measurement method according to the invention.

FIG. 1 shows the arrangement of a first embodiment of the ultrasonic speckle velocity measurement method according to the invention. This invention is characterized by regarding a moving member as an aggregation of microscopic scattering bodies, detecting the result of random interference between waves scattered by the microscopic scattering bodies, i.e., speckles, to measure velocity, to thereby detect the state of movement of the moving members without using the conventional Doppler method.

With reference to FIG. 1, in a transmission step 100 an ultrasonic pulsed wave or ultrasonic continuous wave is transmitted into a subject. In terms of the apparatus, the ultrasonic wave is transmitted by a transmitter 10 toward a blood vessel 22 in which there is a flow of blood 15 that contains an aggregation of microscopic scattering bodies (for example blood. corpuscles). In a reception step 101 the echoes reflected by the blood 15, i.e., ultrasonic scattered wave reflections, are received by a receiver 12, and the process advances to an amplitude detection step 102.

In the amplitude detection step 102 the time-based fluctuations of the echo signal obtained in the reception step 101 are detected as, for example, envelope fluctuations. The process then advances to a frequency analysis step 103.

In the frequency analysis step 103 the degree of time-based echo signal amplitude fluctuation is ascertained as, for example, an envelope fluctuation frequency, and this fluctuation frequency is detected. The frequency analysis may be done by differentiating the echo signal amplitude (or envelope curve) relative to time and measuring the zero crossing density of this signal, or the mean value of the amplitude of the echo signals may be subtracted from the amplitude thereof and the zero crossing density of the signals measured.

There are various other methods that can be used to quantify the degree of time-based fluctuation in the amplitude of the echo signal. For example, the power spectrum of the envelope waveform or the statistics thereof, i.e., the mean value, the variance or the higher order moment or the like, can be obtained and used individually or in combination for such quantification.

Next comes the final step, a velocity conversion step 104, in which the velocity is measured from the fluctuation frequency obtained in the frequency analysis step 103. As mentioned above, as the fluctuation frequency is proportional to the velocity, the velocity state of a moving member can be detected from the fluctuation frequency.

Figure 2:
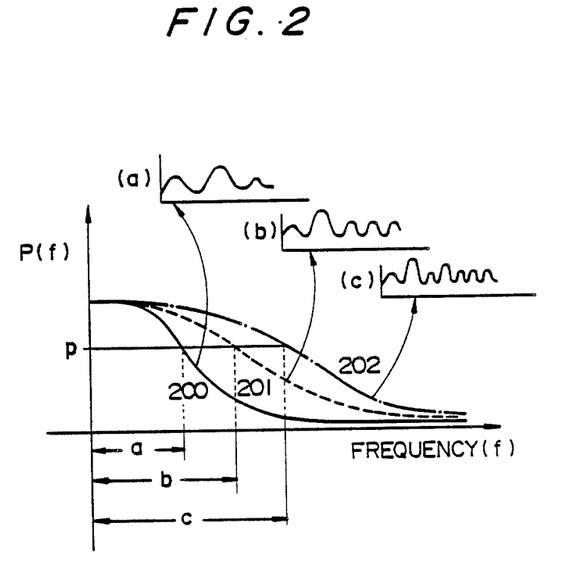
FIG. 2 is .an explanatory diagram showing the relationship between the time-based amplitude variation in echo signals and the power spectrum P(f).

An example of quantification of the degree of amplitude fluctuation from a power spectrum will now be described with reference to FIG. 2, which shows a power spectrum P(f). With respect to the detection of the power spectrum of the echo signal envelope from the microscopic scattering bodies, a curve 200 is obtained when the envelope fluctuation is gentle, as shown by (a); a curve 201 is obtained when the envelope fluctuation is relatively intense, as shown by (b); and a curve 202 is obtained when the envelope fluctuation is intense, as shown by (c). Thus, there is an increase in the high-frequency component of the power spectrum that corresponds to the intensity of the fluctuation.

Therefore, the velocity state can be estimated by detecting frequency widths a, b, c of an intensity p in this power spectrum. Also, for cases where the relationship between frequency widths and velocity is not proportional, if frequency widths for a known movement velocity V are measured beforehand and an approximation equation used to obtain the relationship of frequency widths to velocity V, this approximation equation can be used to calculate the velocity V.

Figure 3:
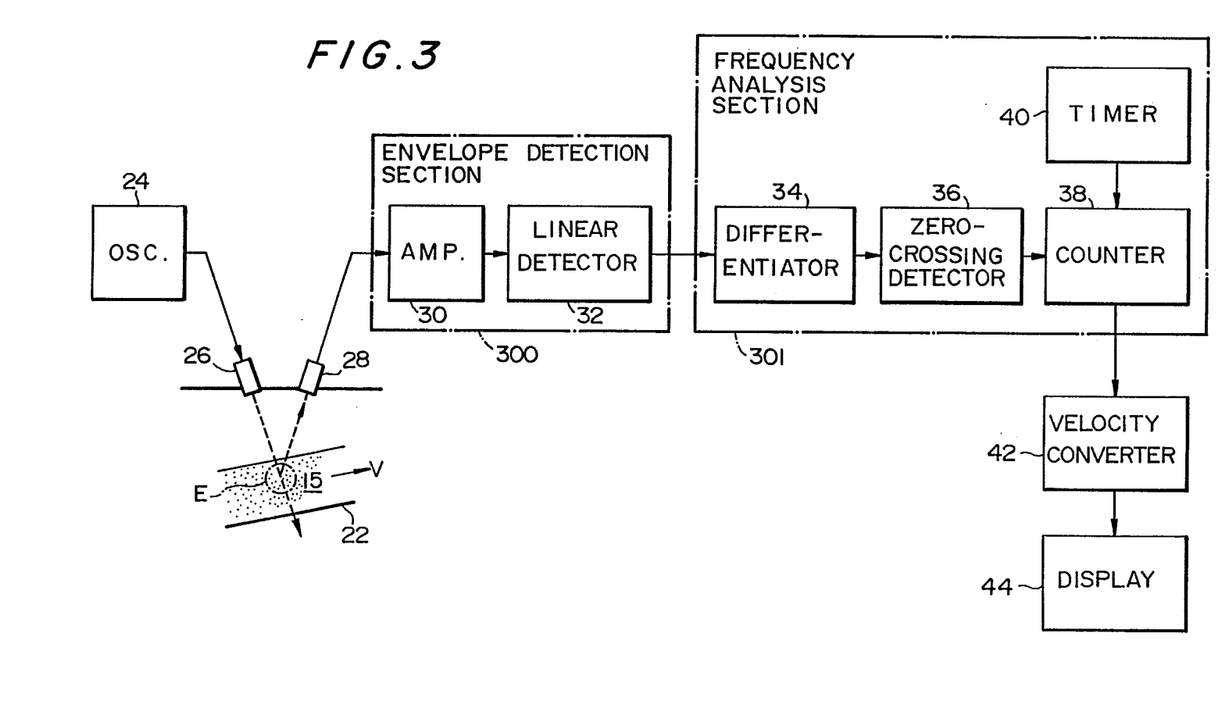
FIG. 3 is a block circuit diagram of a second embodiment of the ultrasonic speckle velocity measurement apparatus according to the invention.

With the apparatus of the invention, a second embodiment in which an ultrasonic continuous wave is used will now be described, with reference to FIG. 3. In FIG. 3, a transmission section is constituted of an oscillator 24 that produces a fixed-frequency transmission signal and a transmission transducer 26. An ultrasonic continuous wave is transmitted from the transmission transducer 26 toward a blood vessel 22 in which there is a flow of blood 15 constituted of a large number of microscopic scattering bodies.

When an ultrasonic continuous wave is used, a separate transducer, i.e., reception transducer 28, is provided by means of which an echo signal reflected from the interior of the blood vessel 22 can be received. Is this case, the spatial location at which the movement velocity is measured is determined from the directivity and positional relationship of the transmission transducer 26 and reception transducer 28. That is, if the transmission transducer 26 and reception transducer 28 have sharp directivity toward the front direction, the point E at which the central axes of the transmission transducer 26 and reception transducer 28 intersect will form the measurement location.

The echo signal obtained by the reception transducer 28 is output to an envelope detection section 300, which is constituted of an amplifier 30 and a linear detector 32. The amplifier 30 amplifies the output of the reception transducer 28 by a prescribed amplification factor and the output is then detected by the linear detector 32, whereby the envelope of the echo signal can be detected. The envelope detection section 300 may be constituted by any other known circuit arrangements that will demodulate an amplitude-modulated signal.

The output from the envelope detection section 300 is supplied to a frequency analysis section 301, which is constituted of a differentiator 34, a zero-crossing detector 36, a counter 38 and a timer 40. The time derivative (differential value) of the envelope of the echo signal output by the linear detector 32 is detected by the differentiator 34. At the zero-crossing detector 36, the portions at which the time derivative becomes zero, i.e., with respect to the envelope curve, the peak and trough portions, are detected and counted by the counter 38. A high-pass filter that filters out direct-current components in the input signal may be used in place of the differentiator 34. In such a case, a count substantially equal to that obtained with the differentiator 34 can be obtained by using the counter 38 to count the number of crossings over the amplitude mean values.

The counter 38 counts at prescribed unit time periods set by the timer 40, which enables the envelope fluctuation frequency to be detected. Connected to the frequency analysis section 301 is a velocity converter 42 that constitutes a velocity conversion section. The fluctuation frequency detected by the frequency analysis section 301, namely the count value N of the counter 38 and moving member movement velocity V are shown by $$V = \gamma N \quad (1)$$

where $\gamma$ is the proportional constant, the magnitude of the envelope fluctuation frequency being proportional to the velocity. Therefore, if on the basis of equation (1) the count value N is converted to the velocity by the velocity converter 42, it becomes possible to determine the velocity of movement of the blood 15.

The output of the velocity converter 42 is supplied to a display 44 whereby the velocity is displayed on the screen thereof. The frequency analysis section 301 detects the envelope amplitude fluctuation frequency by counting the peaks and troughs in the waveform; however, analysis may instead be based on the power spectrum of the echo signal waveform as shown in FIG. 2, or on the statistics . thereof. This second embodiment can provide accurate detection of the velocity information from ultrasonic continuous waves.

Figure 4:
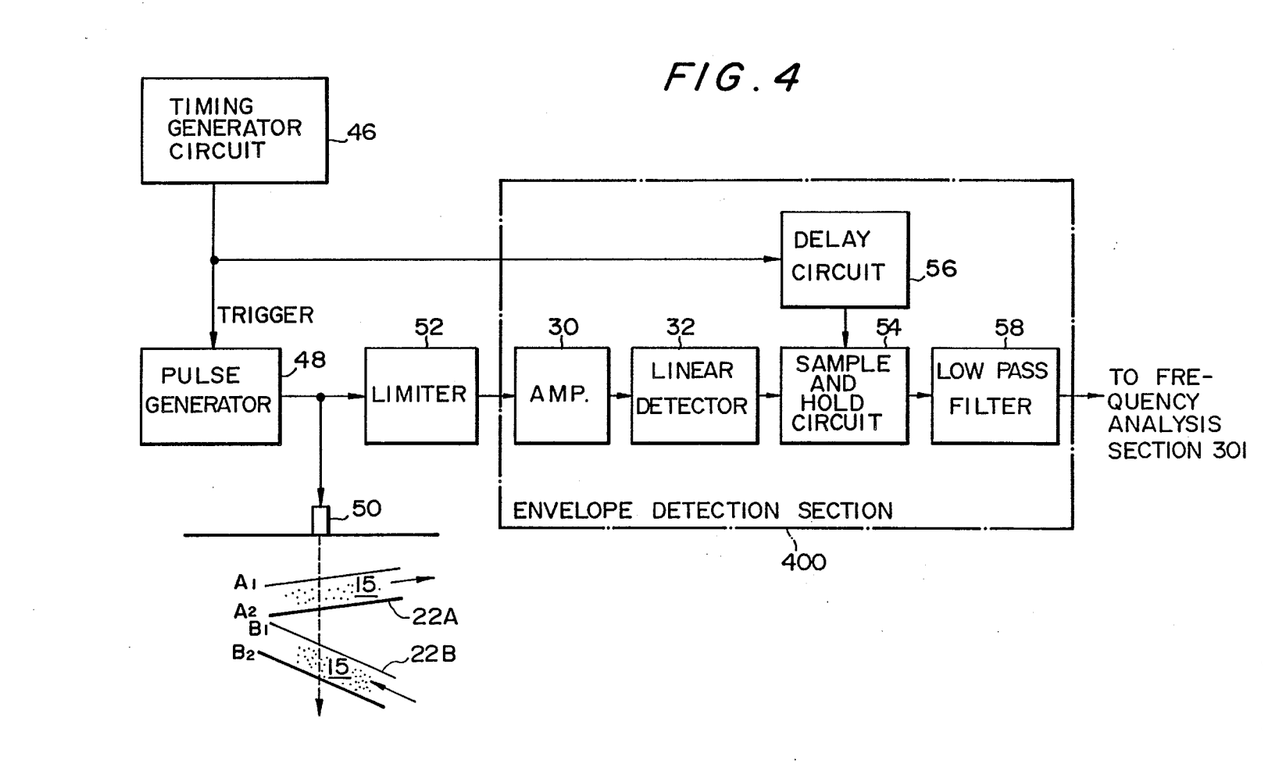
FIG. 4 is a block circuit diagram showing the arrangement of a third embodiment of the ultrasonic speckle velocity measurement apparatus according to the invention.

With the apparatus of the invention, a third embodiment in which an ultrasonic pulsed wave is used will now be described, with reference to FIG. 4. In FIG. 4, a transmission section is constituted of a timing generator circuit 46 for generating ultrasonic pulsed waves at a prescribed repetition frequency; a pulse generator 48 for generating pulse signals in accordance with trigger signals from the timing generator circuit 46; and a transmit-and receive transducer 50 for transmitting and receiving signals. From the transmit-and-receive transducer 50, an ultrasonic pulsed wave is transmitted at a fixed repetition frequency toward blood vessels 22A and 22B.

In the case of ultrasonic pulsed waves, a single transducer is used for both transmission and reception. Here, the transmit-and-receive transducer 50 receives the echo signals reflected from the blood 15 in the blood vessels 22. A limiter 52 is provided so that when the transmit-and-receive transducer 50 that receives the echo signals is being driven, the high voltage generated is not directly applied to the following envelope detection section 400.

When an ultrasonic pulsed wave is being used the envelope detection section 400 connected to the limiter 52 is constituted of an amplifier 30 and linear detector 32 which are also used in the ultrasonic continuous wave configuration; a sample and hold circuit 54 for sampling and holding only .prescribed signals from the linear detector 32; a delay circuit 56 that instructs the sample and hold circuit 54 to take in signals; and a low pass filter 58 that smoothes the output of the sample and hold circuit 54 by removing high-frequency components from the said output and passing low band frequency components.

Following linear detection of the output of the limiter 52, the envelope detection section 400 samples and holds only depthwise prescribed signal settings, enabling velocity information at a selected depth location to be detected.

Described in the above is the arrangement of the envelope detection section 400 when the ultrasonic wave is pulsed. The following frequency analysis section that is connected to the envelope detection section 400 is the same as the one shown in FIG. 3. The operation of the envelope detection section 400 of the third embodiment will now be described with reference to FIG. 5.

Figure 5:
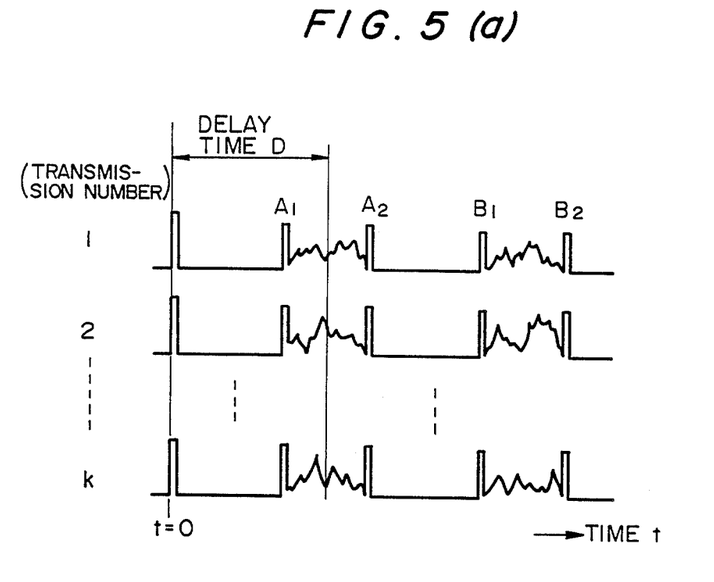
FIG. 5 is a waveform diagram for explaining the operation of the envelope detection section of the apparatus shown in FIG. 4.

FIG. 5 shows the signal processing state of the envelope detection section 400. FIG. 5 (a) shows signals received from each of the transmitted ultrasonic waves, from No. 1 to No. k. These are the envelope signals, formed by the linear detector 32, of the echoes reflected by both of the blood vessels 22A and 22B shown in FIG. 4.

The echo signals $A_1$, $A_2$, $B_1$, $B_2$ reflected from the walls of the blood vessels 22A and 22B appear, in turn, in an order proceeding from the one nearest to the transmit-and-receive transducer 50. If the transmit-and-receive transducer 50 is a distance l from the walls of the vessels, the time at which the echo signals appear will be $2l/c$, where c is the velocity of sound. An envelope of echo signals reflected by the blood 15 is formed between the above-mentioned signals $A_1$ and $A_2$, and $B_1$ and $B_2$ and it appears as a product of interference between scattered waves from groups of scattering bodies (groups of blood corpuscles) within a certain range in the vessels 22A and 22B. In the case of an ultrasonic pulsed wave, the scattered waves that participate in the interference are only those coming from within a distance d corresponding to the pulse duration time $\tau$. Namely, because the interference is only raised within a distance given by $d = c\tau/2$, the time-based amplitude fluctuation at a time-point at which there has elapsed the time required for the ultrasonic pulsed wave to propagate to, and return from, a prescribed position between the blood vessel walls $A_1$ and $A_2$, and $B_1$ and $B_2$, will represent the movement velocity at the position corresponding to that time-point. In this third embodiment, therefore, it becomes possible to obtain velocity information for a prescribed depth by extracting an envelope signal after a prescribed time has passed from the time-point at which the ultrasonic pulsed wave is transmitted.

Specifically, .the delay circuit 56 applies to the sample and hold circuit 54 a delay time D from ultrasonic pulsed wave transmission time $t=0$ corresponding to a prescribed depth position within the subject, and in the received signals of FIG. 5 (a), the portions of the envelope amplitude signal following the delay time D are held in an order of signal reception corresponding to the transmission number.

As shown in FIG. 5 (b), the output of the sample and hold circuit 54 is obtained as a step-shaped waveform of the envelopes of echo signals from prescribed depth positions within the subject, in the transmission number sequence. These form envelope signals produced by interference between scattered waves from groups of microscopic scattering bodies in certain limited regions (within the extent of the above-mentioned distance d) in the blood vessels 22, which are output as time elapses. Here, if Dt represents the time intervals at which trigger signals are output from the timing generator circuit 46 shown in FIG. 4, in FIG. 5 (b) the time of one transmission number will be a time corresponding to Dt.

With this arrangement, by changing the delay time D of the delay circuit 56 the measurement depth position can be changed with ease, enabling the operator to select any depth required.

The step-shaped output of the sample and hold circuit 54 is converted to a smooth waveform by the low pass filter 58. The output of the low pass filter 58 shows the time-based fluctuation of the envelope at the selected prescribed depth position, namely, a position represented by D·c/2, and by frequency-analysis thereof the velocity at the prescribed depth can be obtained.

Frequency analysis can be performed using the same arrangement as that of the frequency analysis section 301 shown in FIG. 3. By using the frequency analysis section 301 to obtain the envelope fluctuation frequency, the blood flow velocity can be displayed on the display 44, via the velocity converter 42.

The above low pass filter 58 is required when the arrangement of the frequency analysis section 301 of FIG. 3 is used. If frequency analysis is done by a method that uses discrete data, such as is represented by fast Fourier transforms, the low pass filter 58 will not be required.

With the apparatus according to this invention, the envelopes are extracted at fixed time intervals elapsed from the time-point at which an ultrasonic pulsed wave is transmitted. Instead of the analogue processing used in this embodiment, digital processing may be used also for holding the envelope.

The third embodiment has a number of advantages, as described below. With the second embodiment, which relates to an ultrasonic continuous wave, it is only possible to obtain velocity information at a location that is decided by the positional relationship of the two transducers; if a plurality of velocity information is required it is necessary to alter the geometrical positions of both transducers. With the third embodiment, however, it is possible to obtain a plurality of velocity information in the direction of the axis of the ultrasonic beam without changing the position of the transmit-and-receive transducer 50.

The invention as described in the foregoing can be applied to ultrasonic diagnostic apparatuses. In the case of such an application, the display 44 could be used to display velocity information as well as tomographic images. It would be possible, for example, to numerically display velocity values of a prescribed point selected from a tomographic image or overlay velocity information on a tomographic image, enabling the blood flow in a living subject to be depicted explicitly on a screen.

As has been described in the foregoing, the advantages of this invention, whereby a moving member is regarded as an aggregation of microscopic scattering bodies and time-based fluctuations in echo signal amplitude that appear as the result of interference between waves scattered by the microscopic scattering bodies are detected, are that the velocity of moving members can be detected without using the conventional ultrasonic wave Doppler method, and it is possible to accurately measure low velocities and detect velocities in directions which are perpendicular to the ultrasonic wavebeam, which could not be detected with the said ultrasonic wave Doppler method.

Moreover, using the apparatus of this invention for ultrasonic continuous waves enables movement velocities at a position decided by the two transducers used (one for transmission and one for reception) to be detected with good accuracy. In addition to this, when an ultrasonic pulsed waves is used, movement velocity at a selected prescribed depth location can be accurately detected using a single transducer for transmitting and receiving, and from the information thus detected, an image of the state of motion of a moving member inside a live subject can be displayed.

What is claimed is:

1. A non-Doppler ultrasonic speckle velocity measurement method comprising the steps of:
    transmitting ultrasonic waves toward a moving measurement object including a large number of microscopic scattering bodies;
    receiving echo signals generated by the interference of scattering waves reflected from said scattering bodies;
    detecting the envelope of the time-based amplitude fluctuation of said echo signals;
    frequency-analyzing said envelope of the time-based amplitude fluctuations to detect a fluctuation frequency showing the degree of said fluctuation; and
    computing the speckle velocity from the fluctuation frequency.

2. A method according to claim 1 wherein said frequency-analyzing step detects the degree of the time-based amplitude fluctuation from a power spectrum of the envelope of the time-based echo signal amplitude fluctuation wave form or from the statistics thereof.

3. A non-Doppler ultrasonic speckle velocity measurement apparatus comprising:
    means for transmitting an ultrasonic continuous wave toward a measurement object including a large number of microscopic scattering bodies;
    means for receiving echo signals generated by the interference of scattering waves reflected from said scattering bodies;
    means for detecting the envelope of the time-based fluctuation in amplitude of said echo signals:
    means for frequency-analyzing said envelope of the time-based fluctuation in amplitude to detect a fluctuation frequency showing the degree of said fluctuations; and
    means for computing the speckle velocity from the fluctuation frequency.

4. A non-Doppler ultrasonic speckle velocity measurement apparatus comprising:
    means for transmitting an ultrasonic pulsed wave toward a measurement object including a large number of ultrasonic scattering bodies;

means for receiving echo signals generated by the interference of scattering waves reflected from said scattering bodies;

means for detecting the envelope or the time-based signals at a selected location within the subject by amplifying the echo signals to obtain the envelope and sample-holding the selected signal within the envelope;

means for frequency-analyzing the envelope or time-based fluctuation in amplitude to detect a fluctuation frequency showing the degree of said fluctuation; and means for computing the speckle velocity from the fluctuation frequency.

5. An apparatus according to claim 3 or 4 wherein said frequency-analyzing means comprises:

a differentiator for differentiating the envelope signal;

a zero-crossing detector for detecting outputs going to zero from among the outputs of the differentiation; and a counter of counting the number of outputs of the zero-crossing detector per unit time.

6. A non-Doppler ultrasonic speckle velocity measurement apparatus according to claim 3 or 4 wherein said frequency analyzing means comprises:

a high-pass filter that removes direct current components from the envelope signal;

a zero-crossing detector detecting outputs going to zero from among the outputs of the filter; and a counter for counting the number of outputs of the zero-crossing detector per unit time.

7. A non-Doppler ultrasonic speckle velocity measurement apparatus according to claim 3 or 4 applied as an ultrasonic diagnostic apparatus wherein detected velocity information is displayed on the display in numerical form and/or in an image form superimposed on a tomographic layer.

8. A non-Doppler ultrasonic speckle velocity measurement apparatus according to claim 5 applied as an ultrasonic diagnostic apparatus wherein detected velocity information is displayed on the display in numerical form and/or in an image form superimposed on a tomographic image.

9. A non-Doppler ultrasonic speckle velocity measurement apparatus according to claim 6 applied as an ultrasonic diagnostic apparatus wherein detected velocity information is displayed on the display in numerical form and/or in an image form superimposed on a tomographic layer.

* * * * *